US011000587B2

(12) United States Patent
Choi

(10) Patent No.: US 11,000,587 B2
(45) Date of Patent: May 11, 2021

(54) USE AS IMMUNE ENHANCER OR PHARMACEUTICAL COMPOSITION FOR TREATMENT OF DEMENTIA, COMPRISING PHYTOSPHINGOSINE-1-PHOSPHATE OR DERIVATIVE THEREOF

(71) Applicant: AXCESO BIOPHARMA CO., LTD., Anyang-si (KR)

(72) Inventor: Myeong Jun Choi, Seoul (KR)

(73) Assignee: AXCESO BIOPHARMA CO., LTD., Anyang-si (KR)

( * ) Notice: Subject to any disclaimer, the term of this patent is extended or adjusted under 35 U.S.C. 154(b) by 80 days.

(21) Appl. No.: 16/340,465

(22) PCT Filed: Apr. 7, 2017

(86) PCT No.: PCT/KR2017/003804
§ 371 (c)(1),
(2) Date: May 15, 2019

(87) PCT Pub. No.: WO2017/213341
PCT Pub. Date: Dec. 14, 2017

(65) Prior Publication Data
US 2020/0046829 A1 Feb. 13, 2020

(30) Foreign Application Priority Data
Jun. 8, 2016 (KR) .................. 10-2016-0070824

(51) Int. Cl.
*A61K 39/39* (2006.01)
*A61P 25/28* (2006.01)
*A61K 9/127* (2006.01)
*A61K 31/661* (2006.01)
*A61K 39/00* (2006.01)

(52) U.S. Cl.
CPC .............. *A61K 39/39* (2013.01); *A61K 9/127* (2013.01); *A61K 31/661* (2013.01); *A61K 39/0007* (2013.01); *A61P 25/28* (2018.01); *A61K 2039/55511* (2013.01); *A61K 2039/55555* (2013.01); *A61K 2039/57* (2013.01)

(58) Field of Classification Search
CPC ...... A61K 39/39; A61K 9/127; A61K 31/661; A61K 39/0007; A61K 2039/55511; A61K 2039/55555; A61K 2039/57; A61K 39/00; A61K 2039/6031; A61K 2039/555; A61P 25/28
See application file for complete search history.

(56) References Cited

U.S. PATENT DOCUMENTS

| 2004/0202640 | A1  | 10/2004 | Crandall            |           |
|--------------|-----|---------|---------------------|-----------|
| 2008/0085939 | A1  | 4/2008  | Nieuwenhuizen et al.|           |
| 2012/0150545 | A1* | 6/2012  | Simon ............. | A61B 5/162 |
|              |     |         |                     | 704/270   |

FOREIGN PATENT DOCUMENTS

| EP | 2982678 A1     | 2/2016  |
| KR | 10-1003532 B1  | 12/2010 |
| KR | 10-2013-0094547 A | 8/2013 |
| KR | 10-1340556 B1  | 12/2013 |
| KR | 10-2015-0025286 A | 3/2015 |
| KR | 10-1514970 B1  | 4/2015  |
| WO | 02072082 A1    | 9/2002  |
| WO | 2012/134134 A2 | 10/2012 |

OTHER PUBLICATIONS

Dante J. Marciani, "Alzheimer's disease: Toward the rational design of an effective vaccine", Rev Neuropsiquiatr, 2015, pp. 140-152, vol. 78, No. 3.
Xingxuan He at al., "Deregulation of sphingolipid metabolism in Alzheimer's disease", Neurobiology of Aging, 2010, pp. 398-408, vol. 31.
Jong Kil Lee et al., "Acid sphingomyelinase modulates the autophagic process by controlling lysosomal biogenesis in Alzheimer's disease", The Journal of Experimental Medicine, Jul. 21, 2014, pp. 1551-1570.
Johnatan Ceccom et al., "Reduced sphingosine kinase-1 and enhanced sphingosine 1-phosphate lyase expression demonstrate deregulated sphingosine 1-phosphate signaling in Alzheimer's disease", Acta Neuropathologica Communications, 2014, pp. 1-10, vol. 2, No. 12.
Timothy A Couttas et al., "Loss of the neuroprotective factor Sphingosine 1-phosphate early in Alzheimer's disease pathogenesis", Acta Neuropathologica Communications, 2014, pp. 1-13, vol. 2, No. 9.
Kinga Czubowicz et al., "Ceramide in the Molecular Mechanisms of Neuronal Cell Death. The Role of Sphingosine-1-Phosphate", Mol Neurobiol, Jan. 14, 2014, pp. 1-12.
Zeynab Kolahdooz et al., "Sphingosin-1-phosphate Receptor 1: a Potential Target to Inhibit Neuroinflammation and Restore the Sphingosin-1-phosphate Metabolism", Can J Neurol Sci., 2015, pp. 195-202, vol. 42.
Anne Gomez-Brouchet et al., "Critical Role for Sphingosine Kinase-1 in Regulating Survival of Neuroblastoma Cells Exposed to Amyloid-β Peptide", Molecular Pharmacology, 2007, pp. 341-349, vol. 72, No. 2.

(Continued)

*Primary Examiner* — Snigdha Maewall
(74) *Attorney, Agent, or Firm* — Sughrue Mion, PLLC

(57) ABSTRACT

Disclosed in the present invention are a use as an immune enhancer of phytosphingosine-1-phosphate (P1P), O-cyclic P1P (cP1P), N-acetylphytosphingosine-1-phosphate (NAPS-1-P), and pharmaceutically acceptable salts thereof, and a pharmaceutical composition or vaccine for treating dementia, comprising such substance on the basis of a neuronal cell death inhibitory effect. The substance according to the present invention exhibits an effect of enhancing Th2 immune response and inhibiting Th1 immune response and has an effect of protecting neurons as well, and thus can be useful as an immune enhancer to help the production of antibodies for the development of a dementia vaccine, as well as an agent for preventing or treating dementia.

14 Claims, 5 Drawing Sheets

(56) References Cited

OTHER PUBLICATIONS

Magdalena Gassowska et al., "Sphingosine Kinases/Sphingosine-1-Phosphate and Death Signalling in APP-Transfected Cells", Neurochem Res, Jan. 23, 2014, pp. 645-652, vol. 39.

Paulo Roberto Louzada et al., "Taurine prevents the neurotoxicity of β-amyloid and glutamate receptor agonists: activation of GABA receptors and possible implications for Alzheimer's disease and other neurological disorders", The FASEB Journal, Mar. 2004, pp. 511-518, vol. 18.

Hye Yun Kim et al., "EPPS rescues hippocampus-dependent cognitive deficits in APP/PS1 mice by disaggregation of amyloid-β oligomers and plaques", Nature Communications, Dec. 8, 2015, pp. 1-12, vol. 6.

Ivan Carrera et al., "Novel Immunotherapeutic Procedures for Prevention of Alzheimer's Disease", Drug Designing: Open Access, 2013, pp. 1-3, vol. 2, Issue 2.

Dante J. Marciani, "Development of Alzheimer's Disease Vaccines: a Perspective", Austin Alzheimers J Parkinsons Dis., 2014, pp. 1-4, vol. 1, No. 1.

Jeniter E. Hughes et al., "Sphingosine-1-Phosphate Induces an Antiinflammatory Phenotype in Macrophages", Circulation Research, Apr. 25, 2008, pp. 950-958.

Ivan Carrera et al., "Vaccine Development to Treat Alzheimer's Disease Neuropathology in APP/PS1 Transgenic Mice", International Journal of Alzheimer's Disease, 2012, . 1-18, vol. 2012, Article ID 376138.

Ivan Carrera et al., "Immunocytochemical Characterization of Alzheimer Disease Hallmarks in APP/PS1 Transgenic Mice Treated with a New Anti-Amyloid-β Vaccine", BioMed Research International, 2013, pp. 1-13, vol. 2013, Article ID 709145.

Ivan Carrera et al., "A Comparative Evaluation of a Novel Vaccine in APP/PS1 Mouse Models of Alzheimer's Disease", BioMed Research International, 2015, pp. 1-16, vol. 2015, Article ID 807146.

Shengrong Li et al., "Chemical synthesis of D-ribo-phytosphingosine-1-phosphate, a potential modulator of cellular processes", Journal of Lipid Research, 1999, pp. 117-125, vol. 40.

Sergio Romangnani, "T-cell subsets (Th1 versus Th2)", Annals of Allergy, Asthma, & Immunology, Jul. 2000, pp. 9-18, vol. 85, No. 1.

International Search Report for PCT/KR2017/003804 dated Jul. 10, 2017 [PCT/ISA/210].

* cited by examiner

[FIG. 1]
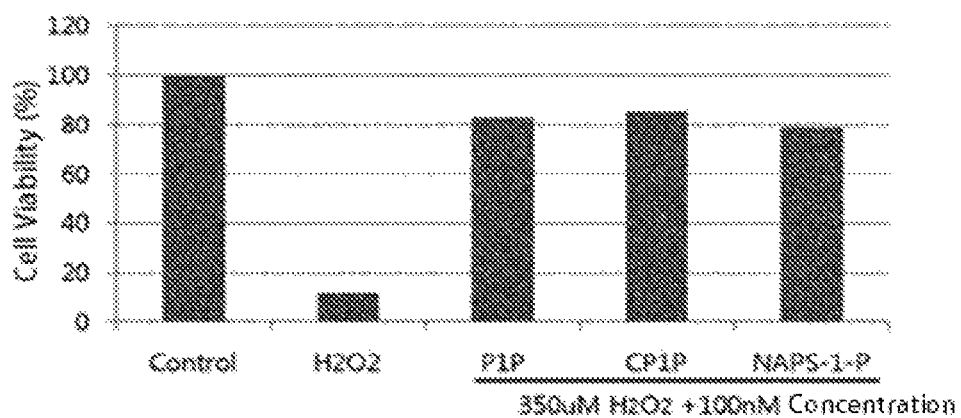
[FIG. 2]
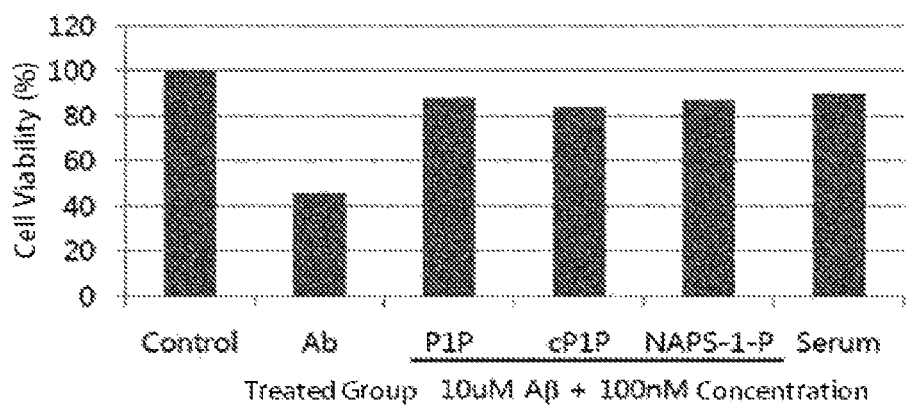

[FIG. 3]
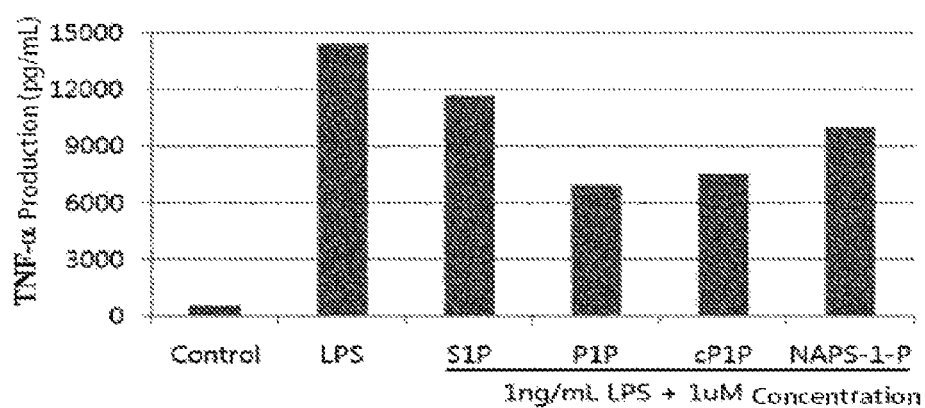

[FIG. 4]
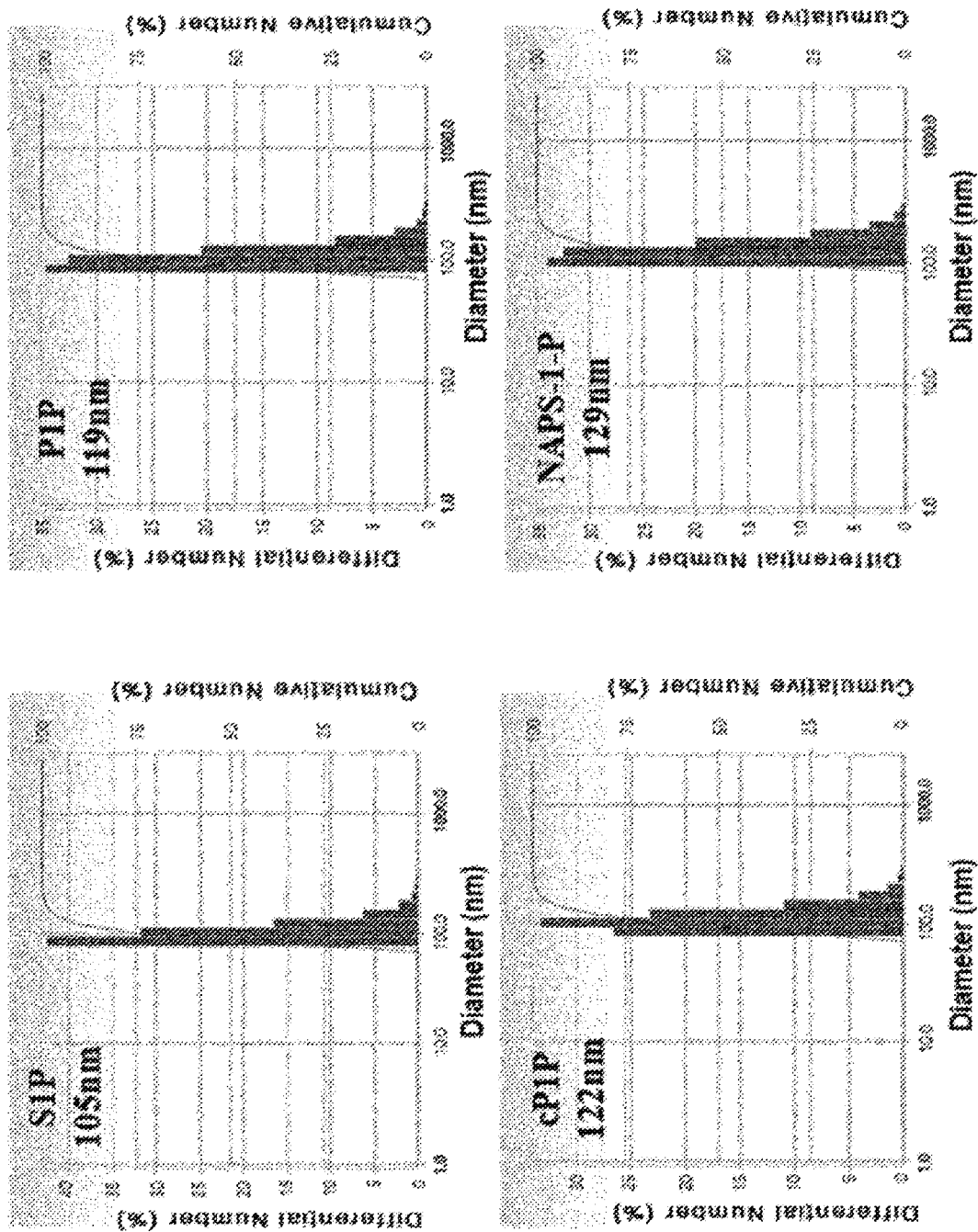

[FIG. 5]
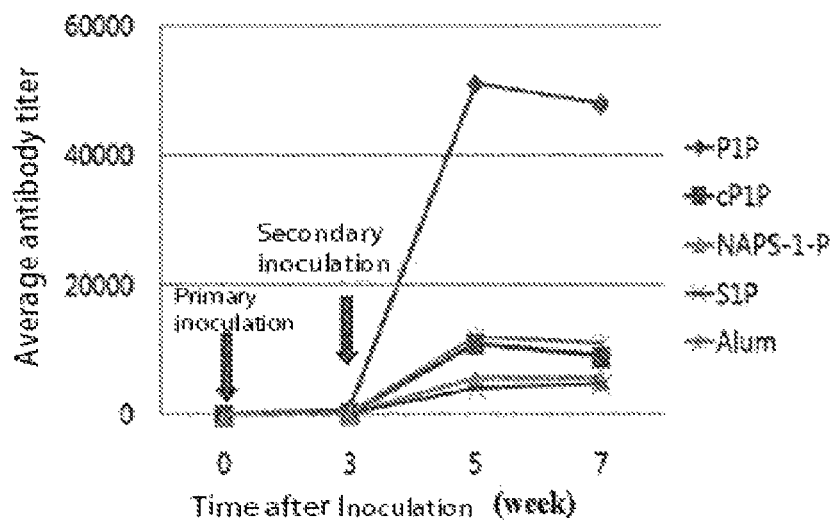
[FIG. 6]
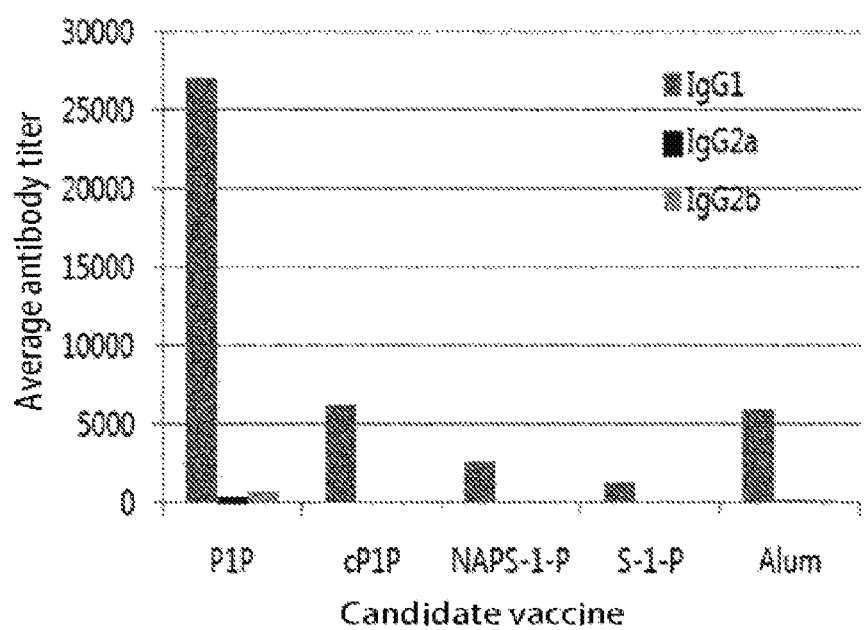

[FIG. 7]
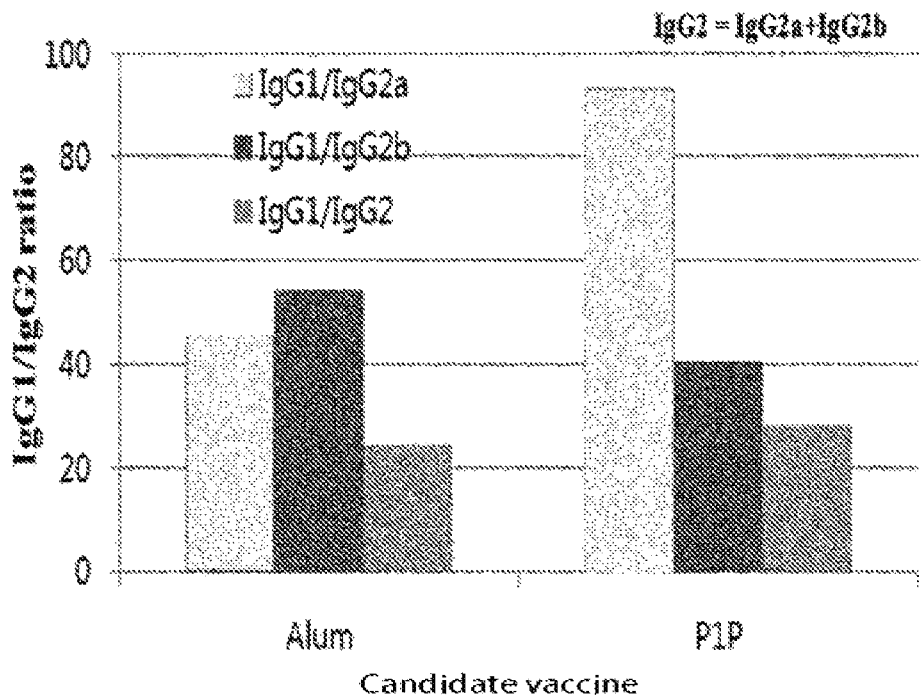
[FIG. 8]
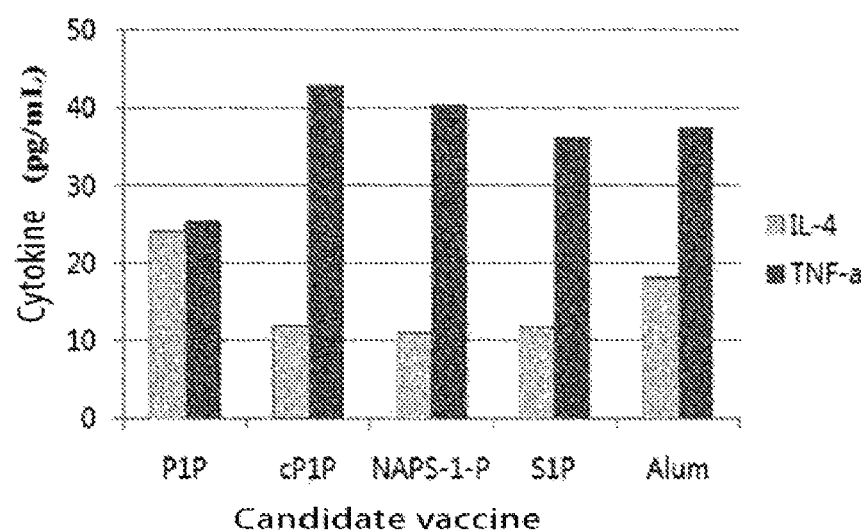

USE AS IMMUNE ENHANCER OR PHARMACEUTICAL COMPOSITION FOR TREATMENT OF DEMENTIA, COMPRISING PHYTOSPHINGOSINE-1-PHOSPHATE OR DERIVATIVE THEREOF

CROSS REFERENCE TO RELATED APPLICATIONS

This application is a National Stage of International Application No. PCT/KR2017/003804 filed Apr. 7, 2017, claiming priority based on Korean Patent Application No. 10-2016-0070824 filed Jun. 8, 2016.

TECHNICAL FIELD

The present disclosure relates to use of phytosphingosine-1-phosphate or a derivative thereof as an immunoadjuvant.

BACKGROUND ART

Vaccines are administered for the prevention or treatment of a specific disease, but in this case, the immune response due to an antigen is insufficient, or often accompanied by an inappropriate response. In this case, an immunoadjuvant (or adjuvant or immune enhancer) is administered together to have an effect on the immunogenicity of the antigen.

Meanwhile, Alzheimer's disease is the most common type of dementia, and is a representative disease among the neurodegenerative disorders. In particular, the most common cause of senile dementia is Alzheimer's disease. Alzheimer's disease initially shows difficulty in remembering recent events and as the disease progress, it is accompanied by various cognitive abnormalities, and all the functions of daily life are lost at the advanced stage.

The cause of onset of Alzheimer's disease is not fully understood at the present time, but it is presumed that amyloid plaques modify normal proteins to form a plaque mass, which leads to loss of the inherent functions. Pathologically, Alzheimer's disease is characterized by general atrophy of the brain, enlargement of the ventricles, neurofibrillary tangles and neuritic (senile) plaques.

Alzheimer's disease is currently one of the ten leading causes of death in the United States, but it is known as the only disease that neither has a preventive or therapeutic therapy nor a way to reduce the speed of progression. Although many therapeutic drugs for Alzheimer's disease have been developed until now, the purpose is to treat symptoms such as memory loss instead of a radical treatment of the disease itself, and experts have evaluated that the developed medicines are not particularly effective. Currently, the number of patients with Alzheimer's disease in the United State is estimated to be more than 5 million, and around 40 million people worldwide have this disease. In particular, about 10% of the 65-year-old elderly people have this disease, and more than 50% of the 85-year-old elderly people have this disease. As the life span of people tends to increase, the number of patients with Alzheimer's disease is expected to increase more, and 80 million people are considered to have this disease by 2040 (Marciani (2015) Rev Neuropsiquiatr, 78: 140-152).

According to Alzheimer's Disease International (ADI), the number of AD patients is expected to increase very rapidly, and is expected to increase to 74.7 million in 2030 and to 131 million in 2050. In addition, the cost of dementia care due to the increase in the number of patients with dementia is estimated to be $818 billion by 2015, and is expected to exceed $2 trillion by 2030.

Therefore, there is a pressing need to develop and improve agents and vaccines for the treatment of dementia.

Recently, in an attempt to treat Alzheimer's disease, therapeutic agents are being developed in a way to: use stem cells, or ameliorate sphingolipid metabolic abnormality in AD patients, or reduce the production of A$\beta$, or prevent hyperphosphorylation of plaques and tau proteins produced by excessively produced A$\beta$. A$\beta$ not only induces the death of neuronal cells but also promotes the formation of ceramide, which is a sphingolipid involved in cell death. The formed ceramide may also promote the production of A$\beta$. Therefore, strategies for degrading the formation of A$\beta$ and plaques are essential (Marciani (2015) Rev Neuropsiquiatr, 78: 140-152; He et al. (2010) Neurobiology of Aging, 31: 398-408).

When examining the changes in sphingolipids of Alzheimer's patients, sphingomyelin (SM) is reduced in the brain of AD patients, and ceramide, a metabolite of SM, is increased. In addition, sphingosine, a degradation product of ceramide, is also increased, and these two substances result in the death of neuronal cells. Also, the content of sphingosine-1-phosphate (S1P), a substance that enhances neuronal survival, is reduced. A$\beta$ activates the enzymes of degrading SM, and degrades SM, thereby increasing ceramide, and subsequently, the ceramide causes oxidative stress, resulting in neuronal cell death and the production of A$\beta$. It is reported that the content of S1P is decreased in the brain of AD patients, so that it does not prevent neuronal cell death, but when the content of S1P is artificially increased, the neuronal cell death can be suppressed and the formation of A$\beta$ can also be reduced. Based on this principle, AD therapeutic agents are being developed using S1P (He et al. (2010) Neurobiology of Aging, 31: 398-408; Lee et al. (2014) J Exp Med, 211: 1551-1570; Ceccom et al. (2014) Acta Neuropathologica Communications, 2: 12; Couttas et al. (2014) Acta Neuropathologica Communications, 2: 9; Czubowicz and Strosznajder (2014) 50: 26-37; Kolahdooz et al. (2015) Can J Neuro Sci, 42: 195-202; Gomez-Brouchet et al. (2007) Molecular Pharmacology, 72: 341-349; Gassowska et al. (2014) Neurochem Res, 39: 645-652).

Attempts have been made to degrade plaques using taurine derivatives in a way to inhibit the formation of A$\beta$ and plaques induced by A$\beta$, and a search is made for plaque-degrading substances (Roberto et al. (2004) FASEB J, 18: 511-518; Kim et al. (2015) Nature Communications, 6: 8997/DOI: 10.1038/ncomms9997). The efficient removal of formation of A$\beta$ and plaques includes a method of producing antibodies against A$\beta$. There have been actively developed vaccines which produce antibodies by administering monoclonal antibodies selectively acting on A$\beta$ or using A$\beta$ as an antigen (Marciani (2015) Rev Neuropsiquiatr, 78: 140-152: Carrera and Cacabelos (2013) Drug Des, 2:2).

In particular, development of an adjuvant that increases the selectivity and immunogenicity of an antigen is needed in order to develop a vaccine for Alzheimer's disease. The most commonly used antigens are A$\beta$ and tau proteins. When A$\beta$ was used as an antigen together with an appropriate adjuvant, antibodies were produced, and the resulting antibodies not only inhibited plaque formation but also was capable of degrading the formed plaques. However, in the case of an AD vaccine, it is essential to develop an adjuvant which enhances a Th2 immune response that enhances antibody production and inhibits a Th1 immune response, which may cause side effects.

The AD vaccine (AN-1792, Elan/Wyeth), which entered clinical trials for the first time, used QS21 as an adjuvant and Aβ as an antigen. As a result, the antibody production was high, but Th1 immunoreactivity was also high. The results revealed that the Th1 immune response could induce an inflammatory reaction as a side effect. Thus, this vaccine has completed the Phase I trial, but the Phase II trial was suspended due to the development of aseptic meningoencephalitis caused by the Th 1 immune response.

Thus, it was necessary to develop an adjuvant which uses a short peptide that does not evoke a Th1 response, or suppresses Th1 and induces a Th2 immune response that helps to produce antibodies. A liposome containing S1P has been developed as an adjuvant that inhibits the Th1 immune response and induces the Th2 immune response by Atlas. An effective vaccine (EB101), which inhibits the Th1 immune response while increasing antibody production has been developed as a result of using whole Aβ as an antigen and a S1P-containing liposome as an adjuvant, and the vaccine has completed animal testing, and the clinical trials are ongoing. The S1P in EB101 vaccine is a useful substance that prevents the neuronal cell death caused by Aβ and oxidative stress, in addition to playing a role in inhibiting the Th1 immune response and inducing Th2 immune response, and is a substance that enables development of effective vaccines without side effects (Marciani (2014) Austin Alzheimers J Parkinsons Dis, 1: 4; Marciani (2015) Rev Neuropsiquiatr, 78: 140-152; Hughers et al. (2008) Circ Res, 102: 950-958; Carrera et al. (2012) International Jouranl of Alzheimer's Disease, volume2012, Article ID 376138, 17 pages; Carrera et al. (2013) BioMed Research International, Volume 2013, Article ID 709145, 12 pages; Carrera et al. (2015) BioMed Research International, Volume 2015, Article ID 807146, 16 pages).

DETAILED DESCRIPTION OF THE INVENTION

Technical Problem

It is one object of the present disclosure to provide use of phytosphingosine-1-phosphate or a derivative thereof as an immune enhancer or a pharmaceutical composition for treating dementia.

Technical Solution

One aspect of the present disclosure provides an immune enhancer, including P1P (phytosphingosine-1-phosphate), cP1P (O-cyclic P1P) or NAPS-1-P (N-acetyl phytosphingosine-1-phosphate), or a pharmaceutically acceptable salt thereof.

The immune enhancer according to the present disclosure is used in a vaccine composition, and P1P (phytosphingosine-1-phosphate), cP1P (O-cyclic P1P), or NAPS-1-P (N-acetyl phytosphingosine-1-phosphate) is contained at a concentration of about 1 μg to 10 mg per vaccine dose.

In another aspect, the immune enhancer according to the present disclosure can be effectively used for the prevention and treatment of dementia through the inhibition of neuronal cell death caused by oxidative stress or amyloid beta and of the Th1 immune response of immune cells, and the promotion of the Th2 immune response. In this respect, a pharmaceutical composition for preventing or treating dementia is provided.

The composition according to the present disclosure may further include amyloid beta, and is provided as a vaccine composition.

The immune enhancer not only induces a Th2 cellular immune response that enhances IL-4 production, but also exhibits a significantly higher humoral immune response in the presence of amyloid beta as an active agent included in the vaccine according to the present disclosure, compared to conventional adjuvants. In particular, the immune enhancer may produce high IgG1 isotype antibodies.

Still another aspect of the present disclosure provides a kit for inhibiting neuronal cell death caused by oxidative stress or amyloid beta in vivo or in vitro, including P1P (phytosphingosine-1-phosphate), cP1P (O-cyclic P1P) or NAPS-1-P (N-acetyl phytosphingosine-1-phosphate), or a pharmaceutically acceptable salt thereof.

Still further another aspect of the present disclosure provides a kit for inhibiting the Th1 immune response of immune cells and promoting the Th2 immune response in vivo or in vitro, including P1P (phytosphingosine-1-phosphate), cP1P (O-cyclic P1P) or NAPS-1-P (N-acetyl phytosphingosine-1-phosphate), or a pharmaceutically acceptable salt thereof.

Still further another aspect of the present disclosure provides a method for inhibiting neuronal cell death caused by oxidative stress or amyloid beta in vivo or in vitro, including treating nerve cells with P1P (phytosphingosine-1-phosphate), cP1P (O-cyclic P1P) or NAPS-1-P (N-acetyl phytosphingosine-1-phosphate), or a pharmaceutically acceptable salt thereof.

Still further another aspect of the present disclosure provides a method for enhancing Th2 immune response and inhibiting Th1 immune response in vivo or in vitro, including treating nerve cells with P1P (phytosphingosine-1-phosphate), cP1P (O-cyclic P1P) or NAPS-1-P (N-acetyl phytosphingosine-1-phosphate), or a pharmaceutically acceptable salt thereof.

Advantageous Effects

The immune enhancer of the present disclosure including one or more compounds selected from the group consisting of P1P (phytosphingosine-1-phosphate), cP1P (O-cyclic P1P), NAPS-1-P (N-acetyl phytosphingosine-1-phosphate), and a pharmaceutically acceptable salt thereof can be effectively used for an AD vaccine composition for inhibiting a Th1 immune response and inducing a Th2 immune response, especially as an vaccine immunoadjuvant for dementia. The immune enhancer may produce high-quality IgG1 isotype antibodies as described in the Examples, by effectively inducing a cellular immune response in the presence of amyloid beta as an active agent included in the vaccine.

The immunoadjuvant according to the present disclosure has superior Th1 immune response inhibiting-ability and antibody producing-ability as compared with S1P, and thus can be particularly used for the development of AD vaccines.

Further, one or more compounds selected from the group consisting of P1P (phytosphingosine-1-phosphate), cP1P (O-cyclic P1P), NAPS-1-P (N-acetyl phytosphingosine-1-phosphate), or a pharmaceutically acceptable salt thereof according to the present disclosure effectively inhibit neuronal cell death caused by oxidative stress or amyloid beta and thus can be effectively used in the treatment or prevention of dementia.

BRIEF DESCRIPTION OF DRAWINGS

FIG. 1 is a graph illustrating a comparison between the efficacies of P1P (phytosphingosine-1-phosphate), cP1P (O-cyclic P1P), and NAPS-1-P (N-acetyl phytosphingosine-1-phosphate) and the efficacy of S1P on the TNF-α production, which is an inflammatory cytokine, after treating with lipopolysaccharide in macrophages.

FIG. 2 is a graph illustrating the efficacies of P1P, cyclic P1P, and NAPS-1-P that protects neuronal cell death induced by oxidative stress.

FIG. 3 is a graph illustrating the protective efficacies of P1P, cyclic P1P, NAPS-1-P and antiserum against neuronal cell death induced by amyloid peptide (Aβ).

FIG. 4 is a graph illustrating the particle distribution of liposomal adjuvants containing S1P, P1P, cyclic P1P, or NAPS-1-P.

FIG. 5 is a graph illustrating the antibody producing-ability of the vaccines prepared in one embodiment of the present disclosure and vaccines including Alum and S1P.

FIG. 6 is a graph illustrating a comparison of the isotypes of antibodies produced against the vaccines prepared in one embodiment according to the present disclosure.

FIG. 7 is a graph illustrating a comparison of the ratio of IgG1/IgG2 of the vaccine including P1P prepared according to one embodiment of the present disclosure and the vaccine including Alum.

FIG. 8 is a graph illustrating the amounts of Th1/Th2 cytokines secreted from splenocytes of vaccine-administered mice prepared in one embodiment of the present disclosure.

DETAILED DESCRIPTION OF THE EMBODIMENTS

The present disclosure is based on the findings that phytosphingosine-1-phosphate or a derivative thereof have the effects of inhibiting the Th1 immune response, promoting production of superior antibodies against immunogenic substances, and protecting neuronal cell death.

Accordingly, in one aspect of the present disclosure, there is provided an immune enhancer, including one or more compounds selected from the group consisting of P1P (phytosphingosine-1-phosphate), cP1P (O-cyclic P1P), NAPS-1-P (N-acetyl phytosphingosine-1-phosphate), and a pharmaceutically acceptable salt thereof.

The P1P (phytosphingosine-1-phosphate, represented by Chemical Formula I below), cP1P (O-cyclic P1P, represented by Chemical Formula II below), and NAPS-1-P (N-acetyl phytosphingosine-1-phosphate, represented by Chemical Formula III below) according to the present disclosure are derivatives of sphingosine-1-phosphate (S1P) and substances that have been developed by the present inventors for various purposes and have been granted patents. They are disclosed in Korean Patent Nos. 10-1003532 and 10-1340556 (Novel substance and use thereof for treating hair loss), and 10-1514970 (Composition for treatment and prevention of atopic dermatitis or skin wounds) and are represented by the following Chemical Formulas I, II and III, respectively.

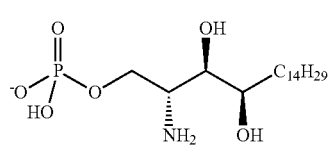

[Chemical Formula I]

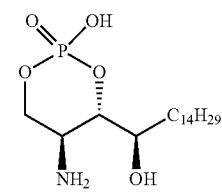

[Chemical Formula II]

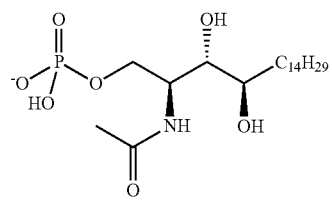

[Chemical Formula III]

The compounds according to the present disclosure may be prepared using common knowledge known in the field of organic chemistry, for example, they may be prepared by the method disclosed in S. Li, W. K. Wilson, G. J. Schroepfer, Chemical synthesis of D-ribo-phytosphingosine-1-phosphate, potential modulator of cellular processes. J. Lipid Res. 40: 117-125, 1999, or by the method disclosed in Korean Patent No. 10-1514970.

The pharmaceutically acceptable salts of the compound of Chemical Formula I, II or III, or solvates thereof may be suitably prepared or selected using knowledge known to those skilled in the art in the field of organic chemistry. As used herein, the salt refers to a salt that is physiologically acceptable and usually does not invoke common allergic or similar reactions when administered to humans. Preferably, the salt may be an acid addition salt formed from a free acid. As the free acid, an organic acid or inorganic acid may be used. The organic acid includes, but not limited to, citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid and aspartic acid. Further, the inorganic acid includes, but not limited to, hydrochloric acid, bromic acid, sulfuric acid, and phosphoric acid. In one embodiment according to the present disclosure, the pharmaceutically acceptable salt may be present as an acid addition salt in which the compound of the Chemical Formula I, II or III forms a salt with a free acid. In addition, the compound of the Chemical Formula I, II or III according to the present disclosure may include not only pharmaceutically acceptable salts, but also all salts, hydrates and solvates that can be prepared by a conventional method. The compound of the Chemical Formula I, II or III may be stabilized by an anion that can be paired with an ammonium cation in the compound, and the anion may be any anion which is pharmaceutically acceptable and can be paired with an ammonium cation, and for example, the anion may be iodide ($I^-$), sulfonate ($SO_3^{2-}$), chloride ($Cl^-$), etc., but is not limited thereto.

The one or more compounds according to the present may be effectively used as a vaccine immune enhancer.

As used herein, the immune enhancer refers to a substance for enhancing immunocompetence which is added to or formulated with an active agent to enhance, induce and/or regulate an immune response to the active agent, and is also known as an adjuvant or immunoadjuvant.

The substance according to the present disclosure may be used, as an active agent, particularly with amyloid beta, which is identified as the cause of Alzheimer's disease. Amyloid beta is the main component of the amyloid plaques found in the brains of the patients with Alzheimer's disease. The amyloid beta may be a peptide composed of amino acids derived from the C-terminus of the amyloid precursor protein (APP), which is a transmembrane glycoprotein. The Aβ is produced as APP is degraded by β- and γ-secretase. The Aβ may be composed of 39 to 43 amino acids, for example 40 to 42 amino acids. For example, the Aβ has been registered as an NCBI accession No. NP_000475 sequence, which is a human-derived amyloid beta A4 protein isoform precursor, and among them, it may be composed of 672 to 713 residues (Aβ42) or 672 to 711 residues (Aβ40). The amyloid beta (Aβ) may be derived from mammals. For example, it may be derived from a human or a mouse.

Accordingly, in another aspect of the present disclosure, there is provided a vaccine composition for preventing Alzheimer's disease or dementia, including amyloid beta as an active agent and one or more compounds selected from the group consisting of P1P (phytosphingosine-1-phosphate), cP1P (O-cyclic P1P), NAPS-1-P (N-acetyl phytosphingosine-1-phosphate), and a pharmaceutically acceptable salt thereof.

As used herein, the term "Alzheimer's disease" refers to a neurodegenerative disease that causes dementia and is a disease that slowly develops and gradually worsens the cognitive functions including memory over time. It includes early-onset (presenile) Alzheimer's disease, which is developed in people less than 65 years of age, late-onset (senile) Alzheimer's disease, which is develop in people over 65 years of age, and familial Alzheimer's disease (FAD). Most of the early-onset Alzheimer's disease appears due to a specific gene mutation, and the familial Alzheimer's disease appears due to a mutation of some genes that are well known to cause Alzheimer's disease.

Since the composition according to the present disclosure inhibits neuronal cell death caused by amyloid beta, it can be used in the prevention and treatment of various types of Alzheimer's disease, which is caused by amyloid beta. The amyloid beta may induce a disease by forming amyloid plaques. The amyloid plaques may be insoluble fibrous protein aggregates including amyloid beta. The amyloid plaques may be present within a cell, on the cell membrane and/or in a space between cells. For example, the amyloid plaques may be present in a space between cells of nerve tissue. The substance according to the present disclosure exhibits an inhibitory effect against neuronal cell death caused by amyloid beta.

As used herein, the term "nervous tissue" includes tissue found in the central nervous system, such as the brain. The brain tissue may include cerebral, cerebellar and hippocampus tissues. The cerebral tissue includes cerebral cortex. The nervous tissue includes not only nervous tissue itself but also nerve cells. The nerve cells are one of the components constituting the nervous tissue. The nerve cells include neurons and/or microglial cells. The culturing of the nervous tissue includes culturing the nerve cells such as neurons and/or microglial cells in vivo or in vitro. The in vivo culture includes culturing of cells in an individual by administering the cells to the individual.

Accordingly, in still another aspect of the present disclosure, there is provided a pharmaceutical composition for preventing or treating Alzheimer's disease or dementia, including one or more compounds selected from the group consisting of P1P (phytosphingosine-1-phosphate), cP1P (O-cyclic P1P), NAPS-1-P (N-acetyl phytosphingosine-1-phosphate), and a pharmaceutically acceptable salt thereof.

In one embodiment of the present disclosure, the pharmaceutical composition according to the present disclosure may be provided in the form of a vaccine, and may further include an active agent capable of preventing dementia, for example, amyloid beta. Antibodies against Aβ are produced through the use of the vaccine, which not only prevents the formation of plaques, but also has a function of degrading the plaques by binding to Aβ. Thus, when the vaccine is used, it may exhibit preventive and therapeutic effects simultaneously.

As used herein, the term "treatment" refers to any behavior that improves or beneficially alters the related symptoms by administration of the composition of the present disclosure. Those skilled in the art will be able to know the precise criteria of the diseases for which the composition of the present disclosure is effective by referring to the materials presented by the Korean Medical Association, and can judge the degree of improvement, enhancement, and treatment of the diseases.

As used herein, the term "prevention" refers to any behavior that inhibits or delays the onset of the related diseases by administration of the composition of the present disclosure. Patients at the stage of predementia exhibiting mild cognitive impairment may be diagnosed using a neuropsychological test. It has been reported that 12% of the patients with mild cognitive impairment progress to Alzheimer's disease in a year on average, and 80% of the patients progress to Alzheimer's disease after 6 years if the mild cognitive impairment remains untreated. Thus, when the composition according to the present disclosure, which can alleviate or reduce toxicity caused by amyloid beta plaques including amyloid beta is administered to patients with mild cognitive impairment, the progression to Alzheimer's disease may be prevented or delayed.

In this regard, the composition of the present disclosure may be prepared as a pharmaceutical composition. The pharmaceutical composition may be administered simultaneously or sequentially and may be used alone or in combination with surgery, or methods of using other pharmaceutical active ingredients and biological response modifiers for the treatment of the aforementioned diseases.

The therapeutic agent or pharmaceutical composition according to the present disclosure may be formulated in a suitable form together with a commonly used pharmaceutically acceptable carrier. As used herein, the 'pharmaceutically acceptable' refers to a composition that is physiologically acceptable and does not cause allergic reactions such as gastrointestinal disorder and vertigo, or similar reactions, when administered to humans. Examples of the pharmaceutically acceptable carriers include carriers for parenteral administration, such as water, suitable oils, saline solution, aqueous glucose, glycol and the like. The composition of the present disclosure may further include stabilizers and preservatives. Suitable stabilizers include antioxidants, such as sodium hydrogen sulfite, sodium bisulfite or ascorbic acid. Suitable preservatives include benzalkonium chloride, methyl- or propyl-paraben, and chlorobutanol. In addition, the composition according to the present disclosure may suitably include suspending agents, solubilizing adjuvants, stabilizers, isotonizing agents, preservatives, adsorption inhibitors, surfactants, diluents, excipients, pH adjusters, analgesic agents, buffers, antioxidants, and the like according to the administration method or the formulation, if necessary. The pharmaceutically acceptable carriers and formulations suitable for the present disclosure, including those exemplified above, are described in detail in the literature [Remington's Pharmaceutical Sciences, latest edition].

The composition of the present disclosure may be formulated using a pharmacologically acceptable carrier and/or excipient according to a method that may be easily performed by those skilled in the art to which the present disclosure belongs and be prepared in a unit dosage form or prepared by intrusion into a multi-dose container. At this time, the formulation may be in the form of oil, a solution in an aqueous medium, a suspension or an emulsion, or it may be in the form of powders, granules, tablets, or capsules.

The administration method of the pharmaceutical composition of the present disclosure may be easily selected according to the formulation, and the pharmaceutical composition may be administered to mammals such as livestock and humans using various routes. For example, the pharmaceutical composition may be formulated in the form of powders, tablets, pills, granules, dragees, hard or soft capsules, liquids, emulsions, suspensions, syrups, elixirs, external preparations, suppositories, and sterilized injection solutions and may be administered systemically or topically, or orally or parenterally. In particular, the parenteral administration may be preferred.

Formulations for parenteral administration include sterilized aqueous solutions, non-aqueous solutions, suspensions, emulsions, lyophilized preparations and suppositories. As the non-aqueous solutions and suspensions, propylene glycol, polyethylene glycol, vegetable oils such as olive oil, injectable esters such as ethyl oleate and the like may be used. As a base for the suppositories, witepsol, macrogol, tween 61, cacao butter, laurin butter, glycerol, gelatin, and the like may be used.

The composition of the present disclosure may be, in particular, administered parenterally (e.g., via intravenous, subcutaneous, intraperitoneal or topical route), depending on the intended method. The dosage may vary depending on the condition and weight of a patient, the severity of disease, the type of drug, the administration route and time, but may be appropriately selected by those skilled in the art.

The composition according to the present disclosure may be administered in a pharmaceutically effective amount. As used herein, the "pharmaceutically effective amount" refers to an amount sufficient to treat diseases, at a reasonable benefit/risk ratio applicable to medical treatment. The effective dosage level of the composition may be determined depending on type of disease, severity of disease, activity of drug, sensitivity to drug, administration time, administration route, excretion rate, treatment duration, factors including drugs used in combination with the composition, and other factors known in the medical field. The composition of the present disclosure may be administered as an individual therapeutic agent or in combination with other therapeutic agents, and may be administered sequentially or simultaneously with conventional therapeutic agents. Also, the composition may be administered in a single or multiple dosage form. It is important to administer the composition in the minimum amount that can exhibit the maximum effect without causing side effects, in view of all the above-described factors, and this amount can be easily determined by those skilled in the art.

Although the dosage of the pharmaceutical composition according to the present disclosure may vary depending on the patient's body weight, age, sex, health condition, diet, administration period, administration method, excretion rate, severity of disease, it may be typically administered at a dose of about 1 ng to 10 mg/day, in particular, about 1 µg to 1 mg/day for an adult with a body weight of 60 kg. Since the dosage may vary depending on various conditions, it will be apparent to those skilled in the art that the dose may be increased or decreased, and thus the dose is not intended to limit the scope of the present disclosure in any way. For example, when the pharmaceutical composition according to the present disclosure is provided as a vaccine, it may be administered for a total of 4 to 5 times once a month. Also, if provided as a vaccine, it may be contained at a dose of 1 µg to 10 mg per vaccine dose. When the pharmaceutical composition is contained at such a concentration, high-quality IgG1 isotype antibodies may be produced as described in the Examples, by effectively inducing a cellular immune response in the presence of an active agent, e.g., amyloid beta, included in the vaccine.

The substance according to the present disclosure can reduce side effects of the active agent or immunogenic composition included in the vaccine by inhibiting the Th1 immune response and promoting the Th2 immune response as described above and as in the experiments of the Examples to be described below. Further, the inhibitory effect against neuronal cell death caused by amyloid beta may inhibit nerve cell or tissue damages.

The Th1 immune response is an adaptive immunity mediated by type 1 CD4+T helper (Th1) lymphocytes, and it is known that Th1 cells produce interferon (IFN)-gamma, interleukin (IL)-2 and tumor necrosis factor (TNF)-beta, and evoke cell-mediated immunity and phagocyte-dependent inflammation (Romagnani S1. Ann Allergy Asthma Immunol. 2000 July; 85(1):9-18).

The Th2 immune response is an adaptive immunity mediated by type 2 CD4+T helper (Th2) lymphocytes, and it is known that Th2 cells produce IL-4, IL-5, IL-6, IL-9, IL-10, and IL-13, evoke strong antibody responses and inhibit inflammation reactions of phagocytic cells (Romagnani S1. Ann Allergy Asthma Immunol. 2000 July; 85(1): 9-18).

Accordingly, in this aspect, the present disclosure relates to a kit for inhibiting the Th1 immune response and promoting the Th2 immune response, or inhibiting neuronal cell death in vitro, including P1P (phytosphingosine-1-phosphate), cP1P (O-cyclic P1P), or NAPS-1-P (N-acetyl phytosphingosine-1-phosphate), or a pharmaceutically acceptable salt thereof.

The active ingredients included in the kit according to the present disclosure may be referred to those mentioned above and the kit may further include additional ingredients for achieving desired effects in vitro and instructions. The kit according to the present disclosure may be used in various ways that require inhibition of the Th1 immune response of the immune cells and promotion of the Th2 immune response, or neuronal cell death.

Cells that can be used for inhibiting the Th1 immune response and promoting the Th2 immune response according to the present disclosure include, but are not limited to, immune cells such as dendritic cells, T cells, or macrophages.

In still further another aspect of the present disclosure, there is provided a method for inhibiting the Th1 immune response of immune cells and promoting the Th2 immune response, or inhibiting neuronal cell death in vitro, including treating nerve cells with P1P (phytosphingosine-1-phosphate), cP1P (O-cyclic P1P), or NAPS-1-P (N-acetyl phytosphingosine-1-phosphate), or a pharmaceutically acceptable salt thereof.

In the method according to the present disclosure, the nerve cells or nervous tissue are as mentioned above, and the step included in the method may be referred to the above-mentioned matters and descriptions of the Examples below.

As a medium related to culturing of nerve cells, any medium widely known to those skilled in the art to which the present disclosure belongs may be used without limitation. The medium may be artificially synthesized, and a commercially prepared medium may be used. Examples of the commercially prepared medium may include DMEM (Dulbecco's Modified Eagle's Medium), MEM (Minimal Essential Medium), BME (Basal Medium Eagle), RPMI 1640, F-10, F-12, α-MEM (α-Minimal Essential Medium), G-MEM (Glasgow's Minimal Essential Medium), IMDM (Isocove's Modified Dulbecco's Medium), and MEF, but are not limited thereto.

The P1P or a derivative compound thereof may be contained at an appropriate concentration depending on the type of intended specific cells as long as it complies with the purpose of the present disclosure.

Hereinafter, Examples are provided to help understanding of the present disclosure. However, these Examples are given for illustrative purposes only to help understanding of the present disclosure, and the scope of the invention is not intended to be limited to or by these Examples.

EXAMPLES

Experiment Methods
Preparation of P1P and Derivatives Thereof
P1P (phytosphingosine-1-phosphate), cP1P (O-cyclic P1P), NAPS-1-P (N-acetyl phytosphingosine-1-phosphate) were prepared as described in Korean Patent No. 1514970.

Preparation of Stock Solutions for Preparation of Liposomal Formulation

Egg phosphatidylcholine (PC) stock solution (PC01): 500 mg of egg phosphatidylcholine was dissolved in 10 mL of chloroform to prepare a 50 mg/mL concentration solution. Cholesterol stock solution (CH01): 100 mg of cholesterol was dissolved in 10 mL of chloroform to prepare a 10 mg/mL concentration solution. S1P stock solution (S1P01, Sigma): 1 mg of S1P was dissolved in methanol to prepare a 1 mg/mL concentration solution. P1P stock solution (P1P01): 10 mg of P1P was dissolved in 10 mL of a chloroform/methanol (2:1) solution to prepare a 1 mg/mL concentration solution. Cyclic P1P stock solution (CP1P01): 10 mg of cyclic P1P was dissolved to prepare a 1 mg/mL concentration solution. NAPS-1-P stock solution (NP01): 10 mg of NAPS-1-P was dissolved to prepare a 1 mg/mL concentration solution.

Preparation of Liposomal (Empty Liposome) Adjuvant Compositions Not Containing Antigen Preparation of Liposomal Adjuvant Containing S1P
300 μL of S1P01 solution, and 1 mL of each of PC01 and CH01 were added to a glass vessel. Then, nitrogen gas was blown over chloroform so that a thin film was formed on the wall of the glass vessel. After the formation of the film, the remaining organic solvent was completely removed by blowing nitrogen gas sufficiently or storing it overnight in a vacuum desiccator. 5 mL of PBS solution was added to the glass vessel and stirred vigorously for 30 minutes. As the lipid film was peeled off, a suspended solution was formed. After the film was completely peeled off and suspended, the solution was treated with sonication, which was repeated 5 times in a manner that the sonication was carried out for 2 minutes and rested for 1 minute, and as a result, a clear solution of the suspended solution was obtained. Then, the solution was centrifuged at 14000 rpm for 5 minutes to remove metallic titanium formed during sonication, and only the supernatant was collected and used in the experiment.

Preparation of Liposomal Adjuvant Containing P1P
300 μL of P1P01 solution, and 1 mL of each of PC01 and CH01 were added to a glass vessel. Then, nitrogen gas was blown over chloroform so that a thin film was formed on the wall of the glass vessel. After the formation of the film, the remaining organic solvent was completely removed by blowing nitrogen gas sufficiently or storing it overnight in a vacuum desiccator. 5 mL of PBS solution was added to the glass vessel and stirred vigorously for 30 minutes. As the lipid film was peeled off, a suspended solution was formed. After the film was completely peeled off and suspended, the solution was treated with sonication, which was repeated 5 times in a manner that the sonication was carried out for 2 minutes and rested for 1 minute, and as a result, a clear solution of the suspended solution was obtained. Then, the solution was centrifuged at 14000 rpm for 5 minutes to remove metallic titanium formed during sonication, and only the supernatant was collected and used in the experiment.

Preparation of Liposomal Adjuvant Containing Cyclic P1P
300 μL of CP1P01 solution, and 1 mL of each of PC01 and CH01 were added to a glass vessel. Then, nitrogen gas was blown over chloroform so that a thin film was formed on the wall of the glass vessel. After the formation of the film, the remaining organic solvent was completely removed by blowing nitrogen gas sufficiently or storing it overnight in a vacuum desiccator. 5 mL of PBS solution was added to the glass vessel and stirred vigorously for 30 minutes. As the lipid film was peeled off, a suspended solution was formed. After the film was completely peeled off and suspended, the solution was treated with sonication, which was repeated 5 times in a manner that the sonication was carried out for 2 minutes and rested for 1 minute, and as a result, a clear solution of the suspended solution was obtained. Then, the solution was centrifuged at 14000 rpm for 5 minutes to remove metallic titanium formed during sonication, and only the supernatant was collected and used in the experiment.

Preparation of liposomal adjuvant containing NAPS-1-P
300 μL of NP01 solution, and 1 mL of each of PC01 and CH01 were added to a glass vessel. Then, nitrogen gas was blown over chloroform so that a thin film was formed on the wall of the glass vessel. After the formation of the film, the remaining organic solvent was completely removed by blowing nitrogen gas sufficiently or storing it overnight in a vacuum desiccator. 5 mL of PBS solution was added to the glass vessel and stirred vigorously for 30 minutes. As the lipid film was peeled off, a suspended solution was formed. After the film was completely peeled off and suspended, the solution was treated with sonication, which was repeated 5 times in a manner that the sonication was carried out for 2 minutes and rested for 1 minute, and as a result, a clear solution of the suspended solution was obtained. Then, the solution was centrifuged at 14000 rpm for 5 minutes to remove metallic titanium formed during sonication, and only the supernatant was collected and used in the experiment.

Preparation of Liposomal (Empty Liposome) Adjuvant Compositions Containing AD Antigen Preparation of Liposomal Adjuvant Containing S1P and AD Antigen 0.9 mL of empty S1P-containing liposome without antigen and 0.1 mL of Aβ solution (Aβ42 peptide fragment: Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala, Sigma, USA) at a concentration of 5 mg/mL were placed in a cryo vial, mixed well and frozen in liquid nitrogen for 30 minutes or more. Subsequently, the mixture was thawed at room temperature, stirred and then frozen again in liquid nitrogen. This procedure was repeated three times to produce a liposomal adjuvant containing the antigen. For an animal experiment, 100 μL of this liposome was administered intramuscularly to the mice.

Preparation of Liposomal Adjuvant Containing P1P and AD Antigen 0.9 mL of empty P1P-containing liposome without antigen and 0.1 mL of Aβ solution at a concentration of 5 mg/mL were placed in a cryo vial, mixed well and frozen in liquid nitrogen for 30 minutes or more. Subsequently, the mixture was thawed at room temperature, stirred and then frozen again in liquid nitrogen. This procedure was repeated three times to produce a liposomal adjuvant containing the antigen. For an animal experiment, 100 μL of this liposome was administered intramuscularly to the mice.

Preparation of Liposomal Adjuvant Containing Cyclic P1P and Aβ Antigen 0.9 mL of empty Cyclic P1P-containing liposome without antigen and 0.1 mL of Aβ solution at a concentration of 5 mg/mL were placed in a cryo vial, mixed well and frozen in liquid nitrogen for 30 minutes or more. Subsequently, the mixture was thawed at room temperature, stirred and then frozen again in liquid nitrogen. This procedure was repeated three times to produce a liposomal adjuvant containing the antigen. For an animal experiment, 100 μL of this liposome was administered intramuscularly to the mice.

Preparation of Liposomal Adjuvant Containing NAPS-1-P and Aβ Antigen 0.9 mL of empty NAPS-1-P-containing liposome without antigen and 0.1 mL of Aβ solution at a concentration of 5 mg/mL were placed in a cryo vial, mixed well and frozen in liquid nitrogen for 30 minutes or more. Subsequently, the mixture was thawed at room temperature, stirred and then frozen again in liquid nitrogen. This procedure was repeated three times to produce a liposomal adjuvant containing the antigen. For an animal experiment, 100 μL of this liposome was administered intramuscularly to the mice.

Measurement of Particle Size of Prepared Liposomal Adjuvants

The particle size of the liposomal adjuvants prepared above was measured by a laser light scattering method using ELS-Z (Otsuka Electronics, Tokyo, Japan) according to the manufacturer's instructions. The particle size of the liposomal adjuvants is expressed by number distribution.

Mouse Vaccination

The mice were inoculated with the vaccines prepared as described above. 6-week-old Balb/c mice were used in the experiment, and there were 4 mice per group. The mice were injected intramuscularly with the vaccines prepared containing PBS, Alum, S1P (EB101), P1P, cyclic P1P, and NAPS-1-P as described above. The vaccines were injected in an amount of 100 μL per mouse, and 100 μL of liposome solution contained about 50 μg of Aβ antigen and about 1.08 mg of lipid (lecithin and cholesterol). The vaccine candidates were inoculated twice at an interval of 3 weeks. PBS was used as a negative control without Aβ antigen, and S1P and Alum were used as control. Alum is an adjuvant used in vaccines and is known to induce a Th2 immune response, and thus was used as a positive control for the Th2 response, and S1P was used as a control for comparison of antibody producing-ability.

Measurement of Antibody-Forming Ability in Mice

As in Example 5, blood was collected 3 weeks after the first inoculation of the vaccine and 2 and 4 weeks after the second inoculation in the mice, and 100 to 150 μl of blood was collected from retro-orbital venous plexus until 2 weeks after the second inoculation. In the fourth week, which was the last week, about 300 to 400 μl of blood was collected from the heart, and the serum components were separated by centrifugation at 1400 rpm for 10 minutes at room temperature. The antibody-forming ability in the serum was determined as follows:

Measurement of Total IgG Content

A 96-well plate was coated with Aβ antigen (1 μg/mL) and reacted at room temperature overnight. Then, the solution in each well was removed and blocked with albumin. The primary antibody (the immune serum) was subjected to 2-fold dilution with the following composition solution (0.014 M sodium phosphate, pH 7.4, 0.15 M NaCl, 0.6% albumin, 0.05% thimerosal) and added to each well. After reacting at room temperature for about 1 hour, the antibodies were washed 5 times with PBS containing 0.05% Tween 20. Subsequently, a secondary antibody conjugated to horseradish peroxidase (goat mouse IgG conjugated to horseradish peroxidase, Boehringer Mannheim) was added and reacted at room temperature for 1 hour. After washing 5 times with PBS containing Tween, 100 μL of 3,3,5,5-tetramethyl benzidine (from Pierce Chemicals) was added for color development, and reacted at room temperature for 15 minutes. The color development reaction was terminated by adding sulfuric acid. Then, absorbance was read with an ELISA plate reader (BioRad 680 ELISA Reader), and the titer of the antibody was calculated as the inverse of the dilution factor with an absorbance of 0.2 or greater.

Measurement of IgG Isotyping

The IgG isotyping was measured in the same manner as the total IgG measurement except that the following antibodies were used as secondary antibodies. For IgG1, IgG2a and IgG2b, anti-mouse IgG1, IgG2a or IgG2b conjugated to horseradish peroxidase (Boehringer Mannheim) were used.

Analysis of Inflammatory Cytokines in Macrophages

Raw264.7 cells, which is a mouse macrophage cell line (Korean Cell Line Bank, cultured with RPMI 1640/10% fetal bovine serum) were seeded at $4.5\times10^5$/mL and cultured overnight, and then, treated with LPS (lipopolysaccharide) (1 ng/mL), and S1P and P1P diluted with a culture medium according to the concentrations (20 nM, 100 nM, 500 nM, 1000 nM). After culturing at 37° C. in a 5% $CO_2$ incubator for 4 hours, the supernatant was collected and stored at 4° C. The concentration of TNF-α, an inflammatory cytokine secreted in the supernatant, was measured using an ELISA kit (BD OptEIA™ TNF Mouse set) according to the manufacturer's instructions. The culture medium was diluted by ¼ in all experimental groups except for the treated group, and the concentration was measured.

Analysis of Th1/Th2 Cytokines in Splenocytes of Inoculated Mice

The spleen was removed from the mice inoculated as described above to obtain splenocytes. Red blood cells were lysed with 100 mM Tris buffer. The obtained splenocytes were washed twice with PBS and centrifuged at 1600 rpm for 5 minutes. The splenocytes were counted and cultured in RPMI 1640 medium containing 10% fetal bovine serum at 37° C. in a 5% $CO_2$ incubator. The splenocytes thus obtained were re-stimulated with a constant amount of Aβ antigen for 72 hours.

Subsequently, Th1 cytokine (TNF-α) and Th2 cytokine (IL-4) secreted from the mouse splenocytes were subjected to an ELISpot assay using an ELISPOT (BD Pharmingen) kit according to the manufacturer's instructions. The number of colored spots was measured to compare the number of cytokine-secreting cells.

Verification of Efficacy in Mouse Neuronal Cell Line (PC12 cell)

PC12 cell line (KCLB 21721, Korea Cell Line Bank, Seoul, Korea) was used to test the effect of P1P and the antibodies on the neuronal cell death caused by hydrogen peroxide and Aβ. The PC12 cells were cultured in RPMI 1640 medium containing 10% fetal bovine serum and 1% penicillin/streptomycin at 37° C. in a 5% $CO_2$ incubator.

After culturing the cells for 24 hours, P1P, cyclic P1P and NAPS-1-P dissolved in DMSO to a concentration of 2 mM were diluted and added to the medium such that the concentrations were 10 nM, 100 nM and 1000 nM. After culturing for 1 hour, 350 μM of $H_2O_2$ was added to stem cells and cultured. Subsequently, in order to measure cell viability, the absorbance was measured at 450 nm using Ez-Cytox (Dogen) after 6 hours, and the efficacy of P1P and derivatives thereof against oxidative stress was measured. The cell death induced by Aβ was initiated by treating 10 μM of Aβ instead of 350 μM of hydrogen peroxide, and the efficacy of P1P and the antibodies against the cell death induced by Aβ was measured using Ez-Cytox after 24 hours.

Example 1. Change in Th1 Cytokines in LPS-Stimulated Macrophage Cell Line

Development of an adjuvant that inhibits the Th1 immune response is essential for the development of an effective AD vaccine. In order to confirm this, an experiment was conducted in which macrophages were stimulated with LPS. When the macrophages were stimulated with LPS, the secretion of TNF-α, a Th1 cytokine, was significantly increased. The results are shown in FIG. 1. As shown in FIG. 1, when stimulated with LPS at a concentration of 1 ng/mL, the secretion of TNF-α, a Th1-type inflammatory cytokine, was significantly increased. In the case of S1P, the secretion of TNF-α tended to decrease slightly in a concentration-dependent manner, whereas, in the P1P-treated group, the secretion of TNF-α tended to decrease significantly in a concentration-dependent manner. In particular, the secretion of TNF-α was significantly reduced in the case of P1P and cyclic P1P (Tables 1-1 to 1-4). As a result of comparing the inhibition rate of TNF-α production at 1000 nM, the rate of inhibition was about 19% in the case of S1P, but the inhibition rate was about 52% in the case of P1P, indicating that Th1 inhibitory effect of P1P was about three times higher than that of S1P. The decrease in the amount of TNF-α means that the immune response induced by Th1 is suppressed. That is, the decrease in the amount of TNF-α means that the effect of suppressing the Th1 immune response is high. Therefore, P1P and cyclic P1P of the present disclosure remarkably suppressed the Th1 immune response compared with S1P. These results indicate that P1P and cyclic P1P substances are substances that suppress Th1 compared to S1P and thus can be more effectively used in AD vaccines.

TABLE 1-1

Th1 Immune Response-Inhibitory Effect of S1P, P1P, cyclic P1P, and NAPS-1-P in LPS-Stimulated Macrophages (10 nM)

| Category | Non-treated Group | LPS-treated Groups ||||
|---|---|---|---|---|---|
| | | Control Group | S1P | P1P | CP1P | NAPS-1-P |
| Amount of TNF-α (pg/mL) | 550 | 14400 | 15000 | 13350 | 10600 | 15000 |
| Inhibition rate of TNF-α production | — | 0% | −4.2% | 7.3% | 26.3% | −4.2% |

TABLE 1-2

Th1 Immune Response-Inhibitory Effect of S1P, P1P, cyclic P1P, and NAPS-1-P in LPS-Stimulated Macrophages (100 nM)

| Category | Non-treated Group | LPS-treated Groups ||||
|---|---|---|---|---|---|
| | | Control Group | S1P | P1P | CP1P | NAPS-1-P |
| Amount of TNF-α (pg/mL) | 550 | 14400 | 13880 | 12500 | 7800 | 15200 |
| Inhibition rate of TNF-α production | — | 0% | −4.2% | 7.3% | 26.3% | −4.2% |

TABLE 1-3

Th1 Immune Response-Inhibitory Effect of S1P, P1P, cyclic P1P, and NAPS-1-P in LPS-Stimulated Macrophages (500 nM)

| Category | Non-treated Group | LPS-treated Groups ||||
|---|---|---|---|---|---|
| | | Control Group | S1P | P1P | CP1P | NAPS-1-P |
| Amount of TNF-α (pg/mL) | 550 | 14400 | 12700 | 10000 | 7500 | 12200 |
| Inhibition rate of TNF-α production | — | 0% | 11.8% | 30.6% | 47.9% | 15.3% |

TABLE 1-4

Th1 Immune Response-Inhibitory Effect of S1P,
P1P, cyclic P1P, and NAPS-1-P in LPS-Stimulated Macrophages
(1000 nM)

| Category | Non-treated Group | LPS-treated Groups | | | | |
|---|---|---|---|---|---|---|
| | | Control Group | S1P | P1P | CP1P | NAPS-1-P |
| Amount of TNF-α (pg/mL) | 550 | 14400 | 116600 | 6940 | 7550 | 10000 |
| Inhibition rate of TNF-α production | — | 0% | 19.0% | 51.8% | 47.5% | 30.6% |

Example 2. Verification of Nerve Cell Protecting-Effect of P1P and Antibodies Since Alzheimer's disease is caused by cell death due to oxidative stress, the efficacy of the P1P substance against the neuronal cell death due to oxidative stress was measured. The results are shown in FIGS. 2 and 3, and it could be confirmed therefrom that all of P1P, cyclic P1P, and NAPS-1-P have an effect of protecting neuronal cell death induced when treated with 350 µM of hydrogen peroxide. When nerve cells were treated with 350 µM of hydrogen peroxide, about 90% of nerve cells were killed, but when the cells were treated with 100 nM of P1P, cyclic P1P, and NAPS-1-P substances, the nerve cells were not killed (FIG. 2). Therefore, P1P and the derivatives thereof have an excellent effect on the protection of nerve cells induced by oxidative stress and thus can be effectively used as a preventive or therapeutic agent for Alzheimer's disease through protecting cell death.

The most important factor in Alzheimer's disease is the accumulation of Aβ, which causes oxidative stress and increase the amount of ceramide, resulting in neuronal cell death. Accordingly, the protective effect against the cell death induced by Aβ was measured. The results are shown in FIG. 3. As shown in FIG. 3, when the nerve cells were treated with 10 µM of Aβ, cell death occurred by more than 50%, but when the cells were treated with P1P and the derivatives thereof, the nerve cells were not killed (FIG. 3). Therefore, P1P and the derivatives thereof have an excellent effect on the protection of nerve cells induced by oxidative stress due to the accumulation of Aβ, indicating that they can be effectively used as a preventive or therapeutic agent for Alzheimer's disease, and in particular, as a preventive agent through protecting cell death.

Further, as shown in FIG. 3, it was found that even when the cells were treated with the mouse serum (serum containing antibodies) immunized with the P1P liposomal adjuvant containing Aβ antigen, the neuronal cell death could be prevented.

The above results indicate that P1P and the derivatives thereof according to the present disclosure have an effect of protecting nerve cells and thus can be effectively used as a preventive or therapeutic agent and also as an adjuvant that assists in antibody production in the development of AD vaccines.

Example 3. Measurement of Particle Size of Liposomal Adjuvants

Liposomes containing S1P, P1P, cyclic P1P, and NAPS-1-P prepared as described in the experimental methods were prepared, and their particle sizes were measured. S1P, and P1P and the derivatives thereof have no effect on the liposome production itself, and liposome particles were well formed regardless of the presence of S1P or P1P. The particle size of the liposomal adjuvants was measured after sonication, and they had a particle size of about 100 to 120 nm regardless of the types of S1P or P1P (FIG. 4).

As shown in FIG. 4, it was found that the particle size of the S1P-containing liposome was about 105 nm, the particle size of the P1P-containing liposome was 119 nm, the particle size of the cyclic P1P-containing liposome was 122 nm, and the particle size of the NAPS-1-P-containing liposome was 129 nm, and that these substances had no effect on the change in the particle size. The adjuvants prepared in the form of liposomes according to the present disclosure showed particularly excellent effects.

Example 4. Measurement of Antibody Producing-Ability

Vaccine candidate substances containing S1P, and P1P and the derivatives thereof were prepared, and the antibody production was confirmed by collecting the mouse blood 3 weeks after the first inoculation, and 2 and 4 weeks after the second inoculation. The results are shown in FIG. 5. As shown in FIG. 5, it was confirmed that the antibody titer was significantly increased after the second inoculation and that the antibody producing-ability was much higher for the P1P-containing vaccine than for the S1P-containing vaccine (FIG. 5, Table 2). These results coincide with the results of immunoassay on the inhibition of the Th1 immune response. In the case of the S1P vaccine candidate, the antibody production was very low and antibody producing-ability was lower than that of Alum used as the positive control. In contrast, the P1P vaccine candidate not only showed the antibody producing-ability higher than that of S1P but also showed the antibody producing-ability much higher than that of Alum used as the positive control. These results indicate that P1P or the derivatives thereof were substances that enhance the nerve cell protecting-effect, reduce side effects by inhibiting the Th1 to be described later, and increase the production of antibodies.

The above results indicate that P1P and the derivatives thereof according to the present disclosure have an effect of protecting nerve cells and thus can be effectively used as a preventive or therapeutic agent and also as an adjuvant that assists in antibody production in the development of AD vaccines.

TABLE 2

Change in average antibody titer of AD candidate vaccines over time after inoculation

| Time | Average Antibody Titer of AD Vaccine Candidates | | | | | |
|---|---|---|---|---|---|---|
| | PBS | Alum | S1P | P1P | CP1P | NAPS-1-P |
| Before inoculation | 0 | 0 | 0 | 0 | 0 | |
| 3 weeks after primary inoculation | 0 | 140 ± 70 | 140 ± 80 | 860 ± 90 | 140 ± 50 | 84 ± 50 |
| 2 weeks after secondary inoculation | 0 | 12000 ± 3000 | 4000 ± 1500 | 51000 ± 1600 | 11000 ± 2500 | 5600 ± 2000 |
| 4 weeks after secondary inoculation | 0 | 11000 ± 3000 | 4800 ± 2000 | 48000 ± 2500 | 9000 ± 2000 | 5600 ± 2000 |

Example 5. Change in Isotype Antibody Titer in AD Vaccine Candidates

IgG1, IgG2a, and IgG2b isotype antibody titers were compared to confirm whether the antibodies produced in Example 4 were produced by the Th1 immune response or the Th2 immune response. The results are shown in FIGS. 6 and 7. IgG2a and IgG2b are produced in large amounts by the Th1 immune response, but IgG1 is produced in a large amount by Th2 immune response. Thus, the Th1/Th2 immune responses can be distinguished by comparing the amounts of IgG1 and IgG2. As a result of comparing IgG1, IgG2a, and IgG2b antibody titers using the blood collected at $4^{th}$ week after the second vaccination, IgG1 was produced in large amounts in both Alum and S1P (Table 3, FIG. 6). In the case of the vaccines composed of P1P or the derivatives thereof, it was also confirmed that IgG1 was produced in large amounts. Further, in the case of P1P, IgG1 production was the highest, and it showed the IgG1 antibody titer 5 to 20 times higher than those of Alum and S1P. Generally, when the Th1 immune response is induced, the ratio of IgG1/IgG2 is lower than 1. However, when the Th2 immune response is induced, the ratio of IgG1/IgG2 is much higher than 1. In fact, the ratio of IgG1/IgG2 in Alum was about 24.6, and the ratio of IgG1/IgG2 in P1P was 28.1 (FIG. 7). Since it is known that Alum produces antibodies by the Th2 immune response, it indicates that P1P, which shows more excellent effects in the antibody production by the Th2 immune response compared to Alum, can be effectively used as an adjuvant of the vaccine composition.

Example 6. Measurement of Production of Th1 Cytokine (TNF-α) and Th2 Cytokine (IL-4)

In the AD vaccines, antibodies exhibit therapeutic effects, and Th1 immune responses may cause side effects, thus, it is necessary to induce the Th2 immune response that assists in the production of antibodies. In order to confirm this, the Th1/Th2 immune responses were compared with splenocytes obtained from the immunized mice. In the case of Alum, which induces the Th2 immune response, IL-4 showed a statistically significant increase, while the increase in TNF-α was statistically insignificant (Table 4, FIG. 8). In contrast, in the case of S1P used in the EB101 vaccine, IL-4 showed a statistically significant increase, but TNF-α did not show a statistically significant increase, and the increase in IL-4 was lower than that of Alum. In the case of the P1P vaccine of the present disclosure, IL-4 showed a statistically significant increase as in the case of Alum, but TNF-α did not show a statistically significant increase. Further, in the case of P1P, the increase in IL-4 was higher than that of Alum and the increase in TNF-α was lower than that of Alum. That is, it can be seen that P1P enhanced the Th2 immune response and suppressed the Th1 immune response compared to Alum.

As a result of examining the inhibitory effect on TNF-α production in an in vitro cell experiment in comparison with S1P, P1P was 3 times more effective than S1P. In an in vivo experiment, P1P was 20 times more effective than S1P in the production of total IgG and IgG1. In addition, in the production of Th2 cytokine, P1P enhanced the production of

TABLE 3

Comparison of Isotype Antibody Titer of AD Vaccine Candidates

| | Average Antibody Titer of AD Vaccine Candidates | | | | | |
|---|---|---|---|---|---|---|
| | PBS | Alum | S1P | P1P | CP1P | NAPS-1-P |
| IgG1 | 0 | 5600 ± 2000 | 1200 ± 430 | 27000 ± 5000 | 6100 ± 2100 | 1700 ± 600 |
| IgG2a | 0 | 130 ± 80 | 0 | 290 ± 120 | 0 | 0 |
| IgG2b | 0 | 110 ± 60 | 0 | 670 ± 200 | 0 | 0 |

Th2 cytokine and conversely, reduced the production of TNF-α due to the Th1 immune response as compared to S1P. Therefore, P1P has the effects of enhancing the antibody production and reducing the Th1 immune response, which can cause a side effect, compared to S1P.

As a result of comparing the pattern of antibody production and cytokine production as described above, it was found that the vaccine containing P1P and the derivatives thereof not only exhibited the effects of enhancing the Th2 immune response and inhibiting the Th1 immune response, but also showed the nerve cell-protecting effect, and thus can be effectively used as a preventive or therapeutic agent for AD and also as an adjuvant that assists in antibody production in the development of AD vaccines.

TABLE 4

Comparison of cytokine production pattern of AD vaccine candidates

| Cytokine (pg/ml) | AD Vaccine Candidate Groups | | | | | |
|---|---|---|---|---|---|---|
| | PBS | Alum | S1P | P1P | CP1P | NAPS-1-P |
| IL-4 | 3.27 ± 1.51 | 18.26 ± 4.25 | 11.84 ± 2.25 | 24.21 ± 5.25 | 12.06 ± 1.25 | 11.04 ± 0.78 |
| TNF-α | 16.85 ± 9.58 | 37.5 ± 13.21 | 36.25 ± 20.15 | 25.5 ± 11.21 | 42.9 ± 15.52 | 40.4 ± 15.52 |

While the exemplary embodiments of the present disclosure have been described in detail, it is to be understood that the scope of the present disclosure is not limited to the disclosed embodiments, but, on the contrary, is intended to cover various modifications and equivalent arrangements made by those skilled in the art using the basic concepts of the present disclosure defined in the following appended claims.

All technical terms used herein have the same meanings that are understood by a skilled person in this art, unless otherwise specified. The contents of all publications disclosed in the present specification as a reference document are incorporated into the present disclosure.

The invention claimed is:

1. A method for treating dementia or inhibiting neuronal cell death caused by oxidative stress or amyloid beta peptide in a subject in need thereof, comprising administering an effective amount of P1P (phytosphingosine-1-phosphate), cP1P (O-cyclic P1P) or NAPS-1-P (N-acetyl phytosphingosine-1-phosphate), or a pharmaceutically acceptable salt thereof to the subject.

2. A method for enhancing Th2 immune response and inhibiting Th1 immune response comprising treating nerve cells of a subject in need thereof, by administering to the subject in need thereof, an effective amount of PIP (phytosphingosine-1-phosphate), cPIP (O-cyclic PIP), or NAPS-I-P (N-acetyl phytosphingosine-1-phosphate), or a pharmaceutically acceptable salt thereof.

3. A method for inhibiting neuronal cell death caused by oxidative stress or amyloid beta peptide in a subject in need thereof, comprising treating nerve cells by administering to the subject in need thereof, an effective amount of PIP (phytosphingosine-1-phosphate), cPIP (O-cyclic PIP) or NAPS-I-P (N-acetyl phytosphingosine-1-phosphate), or a pharmaceutically acceptable salt thereof.

4. The method according to claim 1, which comprises administering a pharmaceutical composition comprising the P1P (phytosphingosine-1-phosphate), cP1P (O-cyclic P1P), NAPS-1-P (N-acetyl phytosphingosine-1-phosphate), or a pharmaceutically acceptable salt thereof.

5. The method according to claim 4, wherein the pharmaceutical composition is a vaccine comprising the PP (phytosphingosine-1-phosphate), cP1P (O-cyclic P1P), NAPS-1-P (N-acetyl phytosphingosine-1-phosphate), or a pharmaceutically acceptable salt thereof at a concentration of 1 μg to 10 mg per vaccine dose.

6. The method according to claim 1, wherein the P1P (phytosphingosine-1-phosphate), cP1P (O-cyclic P1P), NAPS-1-P (N-acetyl phytosphingosine-1-phosphate), or a pharmaceutically acceptable salt thereof is contained in a liposome.

7. The method according to claim 1, which further comprising administering amyloid beta peptide.

8. The method according to claim 1, wherein the subject is afflicted with Alzheimer's disease.

9. The method according to claim 8, wherein the Alzheimer's disease is a presenile Alzheimer's disease, a senile Alzheimer's disease, or a familial Alzheimer's disease.

10. The method according to claim 1, wherein the administering an effective amount of P1P (phytosphingosine-1-phosphate), cP1P (O-cyclic P1P) or NAPS-1-P (N-acetyl phytosphingosine-1-phosphate), or a pharmaceutically acceptable salt thereof to the subject increases a Th2 immune response and/or decreases a Th1 immune response in the subject.

11. A method of vaccination of a subject, comprising administering an immunogenic composition comprising an amyloid beta (AP) antigen in combination with an effective amount of adjuvant to the subject in need thereof, wherein the adjuvant comprises PIP (phytosphingosine-1-phosphate), cPIP (O-cyclic PIP), or NAPS-I-P (N-acetyl phytosphingosine-1-phosphate), or a pharmaceutically acceptable salt thereof.

12. The method of claim 11, wherein the adjuvant is inthe form of a liposome.

13. The method of claim 11, wherein the adjuvant is P1P.

14. The method according to claim 1, which is for inhibiting neuronal cell death caused by oxidative stress or amyloid beta peptide.

* * * * *